United States Patent [19]

Temperilli et al.

[11] Patent Number: 4,785,001
[45] Date of Patent: Nov. 15, 1988

[54] ERGOLINE ESTERS

[75] Inventors: Aldemio Temperilli, Milan; Roberto Maj, Saronno; Sergio Mantegani, Milan; Enzo Brambilla, Mariano Comense, all of Italy

[73] Assignee: Farmitalia Carlo Erba S.p.A., Milan, Italy

[21] Appl. No.: 52,380

[22] Filed: May 21, 1987

[30] Foreign Application Priority Data

May 21, 1986 [GB] United Kingdom ................ 8612366

[51] Int. Cl.$^4$ .................... A61K 31/48; C07D 457/04
[52] U.S. Cl. ........................................ 514/288; 546/67
[58] Field of Search ..................... 546/67, 68; 514/288

[56] References Cited

U.S. PATENT DOCUMENTS

| | | | |
|---|---|---|---|
| 3,879,554 | 4/1975 | Temperilli | 546/68 |
| 3,904,634 | 9/1975 | Arcari et al. | 546/67 |
| 4,057,635 | 11/1977 | Ferrari et al. | 546/67 |
| 4,199,579 | 4/1980 | Ferrari et al. | 546/67 |

FOREIGN PATENT DOCUMENTS

| | | | |
|---|---|---|---|
| 2752533 | 6/1978 | Fed. Rep. of Germany | 546/67 |
| 1363592 | 7/1963 | France | 546/67 |

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

Ergoline Esters having the formula (I)

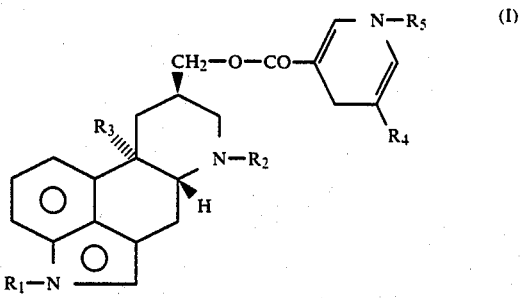

in which $R_1$=H or $CH_3$; $R_2$=$C_1$–$C_4$ hydrocarbon; $R_3$=H or $OCH_3$; $R_4$=H or halogen; $R_5$=$C_1$–$C_4$ alkyl and their pharmaceutically acceptable salts are active at the central nervous system level. A process for their preparation is described.

9 Claims, No Drawings

ERGOLINE ESTERS

BACKGROUND OF THE INVENTION

1. Field of the Invention:

The invention relates to ergoline esters, to a process for their preparation and to pharmaceutical compositions containing them.

2. Discussion of the Background:

Naturally occurring ergot alkloids have been known and used pharmaceutically for many centuries. Naturally occurring ergot alkloids are derivatives of lysergic acid and exhibit profound physiological activity on the nervous system. Synthetic ergot alkloid derivatives can be prepared and have a modified lysergic acid structural framework. There is a continuing need for additional synthetic ergot derivatives which exhibit pharmacological activity in the nervous system and which are useful for treating nervous system disorders.

SUMMARY OF THE INVENTION

Accordingly, one object of the present invention is to provide ergoline derivatives which exhibit pharmacological activity at the central nervous system level and which are useful in treating cerebral metabolic disorders.

Another object of the invention is to provide a method for preparing these ergoline derivatives.

A further object of the invention is to provide a pharmaceutical composition comprising the ergoline derivatives which is useful for treating cerebral insufficiency and senile dementia.

These and other objects of the invention which will become apparent from the following specification have been achieved by the ergoline derivatives of the present invention which have the general formula I

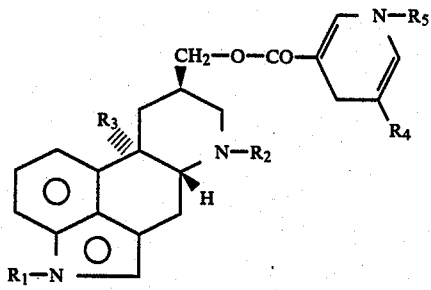

wherein $R_1$ is a hydrogen atom or a methyl group, $R_2$ is a $C_{1-4}$ hydrocarbon group, $R_3$ is a hydrogen atom or methoxy group, $R_4$ is a hydrogen or halogen atom and $R_5$ is a $C_{1-4}$ alkyl group, and pharmaceutically acceptable salts thereof.

The invention also provides a method for the preparation of these ergoline derivatives and pharmaceutical compositions containing them.

DETAILED DESCRIPTION OF THE PREFERRED EMBODIMENTS

The invention provides compounds of the general formula I

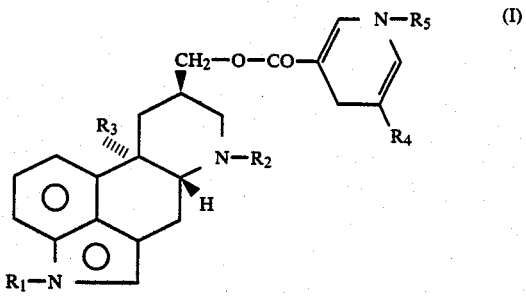

wherein $R_1$ represents a hydrogen atom or a methyl group, $R_2$ represents a hydrocarbon group having from 1 to 4 carbon atoms, $R_3$ represents a hydrogen atom or a methoxy group, $R_4$ represents a hydrogen or halogen atom and $R_5$ represents an alkyl group having from 1 to 4 carbon atoms, and pharmaceutically acceptable salts thereof.

$R_2$ is preferably a methyl, ethyl, n-propyl, i-propyl, butyl, allyl or propargyl group. The term halogen atom encompasses chlorine, bromine, fluorine and iodine. Preferably, however, $R_4$ is a hydrogen, chlorine or bromine atom. $R_5$ is preferably a methyl group.

A particularly preferred compound is 10-methoxy-1,6-dimethyl-8β-(1-methyl-,1,4-dihydro-3-pyridylcarbonyloxymethyl)-ergoline.

The invention further provides a process for the preparation of ergoline esters of the general formula I. This process comprises reducing an ergoline quaternary salt of the general formula II.

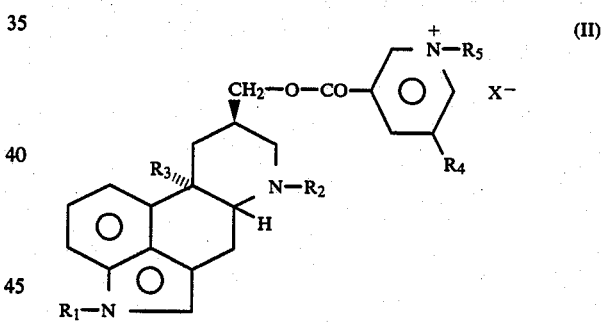

wherein $R_1$, $R_2$, $R_3$, $R_4$ and $R_5$ are defined above and $X^-$ represents a halide anion. Suitable halide anions are chloride, bromide, iodide and fluoride.

The ergoline pyridinium salts of the general formula II may be prepared by quaternization of well known ergoline esters (see U.S. Pat. No. 3,879,554) with alkyl halides.

The reduction occurs specifically in the pyridinium ring to give compounds having general formula I. The reduction is quite specific and under the conditions of the present process does not result in substantial reduction of the other aromatic rings in the molecule.

Suitable reducing agents include complex metal hydrides such as sodium borohydride, sodium dithionite and sodium hydroxymethylsulphoxylate.

The reaction is preferably carried out in an aprotic solvent or in a mildly basic aqueous solution at a temperature of from 5° C. to 25° C. for a period of from 1 to 12 hours, preferably 3 hours.

The ergoline esters according to the invention and their pharmaceutically acceptable salts have remarkable pharmacological activity at the central nervous system level and they may be useful in treating cerebral metabolic vascular disorders.

For example, the compounds increase the local cerebral glucose utilization in the sensomotor cortex e.g., hippocampus, nucleus corpus gentcul, as indicated by the carbon-14-2-deoxyglucose autoradiographic technique with the rat brain on administration i/p. of from about 0.3 to about 30 mg/kg of the compound. For a discussion of the method see, e.g., L. Solokoff, *Journal of Cerebral Blood Flow and Metabolism,* (1), 7–36 (1981); H. E. Savaki et al., *Brain Research,* 233, 347 (1982) and J. McCulloch et al., *Journal Blood Flow and Metabolism,* 1, 133–136 (1981).

The compounds are therefore useful in the treatment of cerebral insufficiency and senile dementia, particularly in the early stages.

For this use, the dosage will, of course, vary depending on the compound employed, mode of administration and treatment desired. However, in general satisfactory results are obtained when administered at a daily dosage of from about 0.01 mg to about 100 mg per Kg animal body weight, conveniently given in divided doses 2 to 4 times a day or in sustained release form. For a larger mammal, the total daily dosage is in the range of from about 1 to about 100 e.g., 1 to 5 mg and dosage forms suitable for oral administration comprise from about 0.2 mg to about 50 mg of the compounds admixed with a solid or liquid pharmaceutical carrier or diluent.

The compounds of the invention may also be administered in the form of a pharmaceutically acceptable acid addition salt. Such salt forms have the same order of activity as the free base forms.

The invention accordingly provides a pharmaceutical composition comprising an ergoline derivative according to the invention in free base form or in pharmaceutically acceptable acid addition salt form in association with a pharmaceutically acceptable carrier or diluent. Such compositions may be formulated in conventional manner so as to be, for example, a solution or a tablet.

The compounds of the invention may be used in an analogous manner to standard compounds used for the treatments mentioned above.

Other features of the invention will become apparent during the course of the following description of an exemplary embodiment which is given for illustration of the invention and is not intended to be limiting thereof.

EXAMPLES

Example 1

10-Methoxy-,1,6-dimethyl-8β-(1-methyl-,1,4-dihydro-3-pyridyl-carbonyloxymethyl)-ergoline (In formula I, $R_1=R_2=R_5=CH_3$, $R_3=CH_3O$, $R_4=H$)

2.5 ml of methyl iodide was added to a solution of 4.42 g of 10-methoxy-,1,6-dimethyl-8β-(3-pyridylcarbonyloxymethyl)-ergoline hydrochloride in 50 ml of dimethylformamide, and the mixture was heated at 50° C. for 5 hours. The yellow material which separated was removed by filtration and washed with dimethylformamide to yield 5.5 g of the quaternary salt melting at 187°–189° C.

To a solution of 4.67 g of this material in 300 ml of degassed 50% aqueous acetone cooled at 5° C., were added 6.78 g of sodium bicarbonate and 13.9 g of sodium dithionite. The mixture was stirred for 3 hours at room temperature. After diluting with water, the separated product was removed by filtration.

The crude material was crystallized several times from acetone-water to give 2 g of the title compound melting at 128°–130° C.

Example 2—Biological Tests

The compound prepared in the Example 1 showed an orientative acute toxicity ($LD_{50}$) higher than 800 mg/Kg (p.o. mice). Moreover, the compound prepared in Example 1 was tested at the dose of 20 mg/Kg p.o. in the rat and the electroencephalographic effects (EEG) were observed. EEG showed increased and long-lasting modifications. See Buonamici, M., Young, G. A. and Khazon (1982), Neuropharmacology, 21 : 825–829.

Obviously, numerous modifications and variations of the present invention are possible in light of the above teachings. It is therefore to be understood that within the scope of the appended claims, the invention may be practiced otherwise than is specifically described herein.

What is claimed as new and desired to be secured by Letters Patent of the United States:

1. an ergoline of the formula

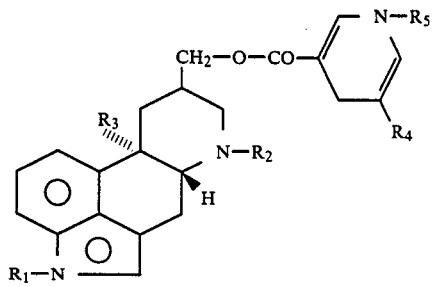

wherein $R_1$ is a hydrogen atom or a methyl group, $R_2$ is one member selected from the group consisting of methyl, ethyl, n-propyl, i-propyl, butyl, allyl, and propargyl groups, $R_3$ is a hydrogen atom or a methoxy group, $R_4$ is a hydrogen or halogen atom, and $R_5$ is a $C_{1-4}$ alkyl group, or a pharmaceutically acceptable salt thereof.

2. The ergoline of claim 1 wherein $R_2$ is selected from the group consisting of a methyl, ethyl, n-propyl, iso-propyl, butyl, allyl and propargyl groups; $R_4$ is selected from the group consisting of hydrogen, bromine, and chloride atoms; and $R_5$ is a methyl group.

3. The ergoline of claim 1, wherein said derivative is 10-methyoxy-1,6-dimethyl-8β-(1-methyl-1,4-dihydro-3-pyridyl-carbonyloxymethyl)-ergoline or a pharmaceutically acceptable salt thereof.

4. A pharmaceutical composition comprising the ergoline of claim 1 in an amount which exhibits pharmacological activity at the central nervous system lever or a pharmaceutically acceptable salt thereof and a pharmaceutically acceptable carrier or diluent.

5. The pharmaceutical composition of claim 4 comprising from about 0.2 mg to about 50 mg of said ergoline or pharmaceutically acceptable salt thereof.

6. The pharmaceutical composition of claim 4, wherein said pharmaceutically acceptable salt is an acid addition salt.

7. The pharmaceutical composition of claim 5, wherein said pharmaceutically acceptable salt is an acid addition salt.

8. The pharmaceutical composition of claim 4, wherein said pharmaceutically acceptable carrier or diluent is a solid.

9. The pharmaceutical composition of claim 4, wherein said pharmaceutically acceptable carrier or diluent is a liquid.

* * * * *